(12) United States Patent
Bange et al.

(10) Patent No.: US 8,185,204 B2
(45) Date of Patent: May 22, 2012

(54) IMPLANTABLE MEDICAL DEVICE TELEMETRY WITH ADAPTIVE FREQUENCY HOPPING

(75) Inventors: Joseph E. Bange, Eagan, MN (US); Vineel Vallapureddy, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 457 days.

(21) Appl. No.: 11/456,937

(22) Filed: Jul. 12, 2006

(65) Prior Publication Data

US 2008/0015655 A1   Jan. 17, 2008

(51) Int. Cl.
 *A61N 1/00* (2006.01)
(52) U.S. Cl. .............................. 607/32; 607/30; 607/60
(58) Field of Classification Search ................... 607/30, 607/32, 60
See application file for complete search history.

(56) References Cited

U.S. PATENT DOCUMENTS

| | | | |
|---|---|---|---|
| 4,633,411 A | 12/1986 | Bliss | |
| 4,799,059 A * | 1/1989 | Grindahl et al. | 340/870.03 |
| 5,342,408 A | 8/1994 | deCoriolis et al. | |
| 5,394,433 A | 2/1995 | Bantz et al. | |
| 5,562,713 A | 10/1996 | Silvian | |
| 5,603,088 A | 2/1997 | Gorday et al. | |
| 5,612,960 A | 3/1997 | Stevens et al. | |
| 5,617,871 A | 4/1997 | Burrows | |
| 5,683,432 A * | 11/1997 | Goedeke et al. | 607/32 |
| 5,729,680 A | 3/1998 | Belanger et al. | |
| 5,752,977 A | 5/1998 | Grevious et al. | |
| 5,843,139 A * | 12/1998 | Goedeke et al. | 607/32 |
| 5,870,391 A | 2/1999 | Nago | |
| 5,887,022 A | 3/1999 | Lee | |
| 6,031,863 A | 2/2000 | Jusa et al. | |
| 6,088,381 A | 7/2000 | Myers, Jr. | |
| 6,130,905 A | 10/2000 | Wakayama | |
| 6,219,580 B1 * | 4/2001 | Faltys et al. | 607/57 |
| 6,223,083 B1 * | 4/2001 | Rosar | 607/60 |
| 6,243,568 B1 | 6/2001 | Detef et al. | |
| 6,381,492 B1 * | 4/2002 | Rockwell et al. | 607/5 |
| 6,424,867 B1 * | 7/2002 | Snell et al. | 607/31 |
| 6,434,429 B1 | 8/2002 | Kraus et al. | |
| 6,443,891 B1 | 9/2002 | Grevious | |
| 6,471,645 B1 * | 10/2002 | Warkentin et al. | 600/300 |
| 6,490,487 B1 | 12/2002 | Kraus et al. | |

(Continued)

FOREIGN PATENT DOCUMENTS

JP   2005-311931 A   11/2005

(Continued)

OTHER PUBLICATIONS

"European Application Serial No. 07840196.5, Response filed Jun. 22, 2011 to Office Action mailed Feb. 22, 2011", 13 pgs.

(Continued)

*Primary Examiner* — Nicole F Lavert
(74) *Attorney, Agent, or Firm* — Schwegman, Lundberg & Woessner, P.A.

(57) ABSTRACT

A far-field radio-frequency (RF) telemetry system transmits data between an implantable medical device and an external system using an active channel selected from a plurality of channels each representing a frequency band within a predetermined frequency range. One or more preferred channels are identified from the plurality of channels based on channel quality indicators produced for each of the channels. When channel hopping is needed, a hop channel is selected from the one or more preferred channels and becomes the active channel.

21 Claims, 7 Drawing Sheets

U.S. PATENT DOCUMENTS

| | | | |
|---|---|---|---|
| 6,535,763 B1* | 3/2003 | Hiebert et al. | 607/32 |
| 6,535,766 B1 | 3/2003 | Thompson et al. | |
| 6,600,952 B1* | 7/2003 | Snell et al. | 607/31 |
| 6,631,296 B1* | 10/2003 | Parramon et al. | 607/61 |
| 6,763,269 B2 | 7/2004 | Cox | |
| 6,801,807 B2 | 10/2004 | Abrahamson | |
| 6,868,288 B2 | 3/2005 | Thompson | |
| 6,897,788 B2* | 5/2005 | Khair et al. | 340/870.16 |
| 6,978,181 B1* | 12/2005 | Snell | 607/60 |
| 6,985,773 B2* | 1/2006 | Von Arx et al. | 607/32 |
| 7,013,178 B2 | 3/2006 | Reinke et al. | |
| 7,146,134 B2 | 12/2006 | Moon et al. | |
| 7,177,700 B1 | 2/2007 | Cox | |
| 7,218,969 B2 | 5/2007 | Vallapureddy et al. | |
| 7,280,872 B1* | 10/2007 | Mosesov et al. | 607/60 |
| 7,289,853 B1 | 10/2007 | Campbell et al. | |
| 7,468,032 B2 | 12/2008 | Stahmann et al. | |
| 7,623,922 B2 | 11/2009 | Bange et al. | |
| 7,787,953 B2 | 8/2010 | Vallapureddy et al. | |
| 7,801,620 B2 | 9/2010 | Freeberg | |
| 7,904,169 B2 | 3/2011 | Bange et al. | |
| 7,959,568 B2 | 6/2011 | Stahmann et al. | |
| 2001/0012955 A1* | 8/2001 | Goedeke et al. | 607/27 |
| 2002/0123672 A1* | 9/2002 | Christophersom et al. | 600/300 |
| 2002/0143372 A1* | 10/2002 | Snell et al. | 607/30 |
| 2002/0183806 A1* | 12/2002 | Abrahamson et al. | 607/60 |
| 2003/0097157 A1* | 5/2003 | Wohlgemuth et al. | 607/27 |
| 2003/0114891 A1* | 6/2003 | Hiebert et al. | 607/32 |
| 2003/0146835 A1 | 8/2003 | Carter | |
| 2003/0187484 A1* | 10/2003 | Davis et al. | 607/60 |
| 2004/0122297 A1 | 6/2004 | Stahmann et al. | |
| 2004/0127959 A1* | 7/2004 | Amundson et al. | 607/60 |
| 2004/0167587 A1* | 8/2004 | Thompson | 607/60 |
| 2004/0176811 A1* | 9/2004 | Von Arx et al. | 607/32 |
| 2004/0176822 A1* | 9/2004 | Thompson et al. | 607/60 |
| 2004/0199221 A1* | 10/2004 | Fabian et al. | 607/60 |
| 2005/0245992 A1 | 11/2005 | Persen et al. | |
| 2006/0013285 A1 | 1/2006 | Kobayashi et al. | |
| 2006/0030903 A1 | 2/2006 | Seeberger et al. | |
| 2006/0161222 A1* | 7/2006 | Haubrich et al. | 607/60 |
| 2006/0161223 A1 | 7/2006 | Vallapureddy et al. | |
| 2006/0195161 A1 | 8/2006 | Li | |
| 2006/0195162 A1 | 8/2006 | Arx et al. | |
| 2007/0049983 A1* | 3/2007 | Freeberg | 607/32 |
| 2007/0185550 A1 | 8/2007 | Vallapureddy et al. | |
| 2008/0262573 A1 | 10/2008 | Seeberger et al. | |
| 2008/0279259 A1 | 11/2008 | Kobayashi et al. | |
| 2010/0036463 A1 | 2/2010 | Bange et al. | |
| 2010/0168819 A1 | 7/2010 | Freeberg | |

FOREIGN PATENT DOCUMENTS

| | | |
|---|---|---|
| JP | 2006-033480 A | 2/2006 |
| JP | 2006-510451 A | 3/2006 |
| JP | 2008-508981 A | 3/2008 |
| WO | WO-98/19400 A1 | 5/1998 |
| WO | WO-2008008564 A2 | 1/2008 |
| WO | WO-2008008564 A3 | 1/2008 |

OTHER PUBLICATIONS

"European Application Serial No. 07840196.5, Office Action mailed Feb. 22, 2011", 4 pgs.

"European Application Serial No. 07840196.5, Response filed Apr. 19, 2010 to Office Action mailed Oct. 22, 2009", 15 pgs.

"Japanese Application No. 2009-519567, Office Action mailed Oct. 21, 2011", 2 pgs.

"Japanese Application No. 2009-519567, Response filed Nov. 9, 2011 to Office Action mailed Oct. 21, 2011", (w/ English Translation of Amended Claims), 9 pgs.

"U.S. Appl. No. 11/039,200 Non Final office action mailed Aug. 3, 2006", 10 pgs.

"U.S. Appl. No. 11/039,200 Notice of allowance mailed Dec. 15, 2006", 4 pgs.

"U.S. Appl. No. 11/039,200 Response filed Nov. 2, 2006 to Non Final office action mailed Aug. 3, 2006", 9 pgs.

Bange, Joseph E., et al., "Implantable Medical Device Telemetry With Periodic Frequency Hopping", U.S. Appl. No. 11/456,942, filed Jul. 12, 2006, 43 Pages.

"U.S. Appl. No. 11/733,339, Interview Summary mailed Aug. 13, 2009", 2 pgs.

"U.S. Appl. No. 12/579,092, Notice of Allowance mailed Sep. 14, 2010", 8 pgs.

"U.S. Appl. No. 12/579,092, Notice of Allowance mailed Oct. 20, 2010", 8 pgs.

"PCT Application No. PCT/US2007/069424, International Search Report mailed Dec. 27, 2007", 4 pgs.

"PCT Application No. PCT/US2007/069424, Written Opinion mailed Dec. 27, 2007", 9 pgs.

"PCT Application No. PCT/US2007/069426, International Search Report mailed Dec. 27, 2007", 4 pgs.

"PCT Application No. PCT/US2007/069426, Written Opinion mailed Dec. 27, 2007", 8 pgs.

Adams, J. T., "An Introduction to IEEE STD 802.15.4", *Aerospace Conference, 2006 IEEE Big Sky*, (Mar. 4-11, 2006), 1-8.

Duflot, M., et al., "A formal Analysis of Bluetooth Device Discovery", *International Journal on Software Tools for Technology Transfer*, 8(6), (2006), 621-632.

Golmie, N., et al., "The Evolution of Wireless LANs and PANs— Bluetooth and WLAN Coexistence: Challenges and Solutions", *IEEE Personal Communications*, 10(6), (Dec. 2003), 22-29.

Zhu, H., et al., "A Survey of Quality of Service in IEEE 802.11 Networks", *Wireless Communications*, 11(4), (Aug. 2004), 6-14.

"U.S. Appl. No. 11/214,508, Response filed Dec. 22, 2008 to Non Final Office Action mailed Sep. 25, 2008", 8 pgs.

"U.S. Appl. No. 11/214,508, Final Office Action mailed Mar. 13, 2009", 8 pgs.

"U.S. Appl. No. 11/456,942, Response filed Nov. 18, 2008 to Non Final Office Action mailed Aug. 18, 2008", 10 pgs.

"U.S. Appl. No. 11/456,942, Final Office Action mailed Mar. 10, 2009", 15 pgs.

"U.S. Appl. No. 11/456,942, Advisory Action mailed May 7, 2009", 6 pgs.

"U.S. Appl. No. 11/456,942, Notice of Allowance mailed Jul. 17, 2009", 13 pgs.

"U.S. Appl. No. 11/456,942, Response filed May 4, 2009 to Final Office Action mailed Mar. 10, 2009", 9 pgs.

"U.S. Appl. No. 11/456,942, Response filed Jun. 4, 2009 to Advisory Action mailed May 7, 2009", 10 pgs.

"U.S. Appl. No. 11/214,508, Non-Final Office Action mailed Sep. 25, 2008", 6 pgs.

"U.S. Appl. No. 11/456,942, Non-Final Office Action mailed Aug. 18, 2008", 15 pgs.

"U.S. Appl. No. 11/214,508, Notice of Allowance mailed May 18, 2010", 4 pgs.

"U.S. Appl. No. 11/214,508, Notice of Allowance mailed Nov. 18, 2009", 4 pgs.

"U.S. Appl. No. 11/733,339, Notice of Allowance mailed Feb. 25, 2010", 6 pgs.

"U.S. Appl. No. 11/733,339, Notice of Allowance mailed Apr. 21, 2010", 6 pgs.

"U.S. Appl. No. 11/733,339, Response filed Dec. 4, 2009 to Non Final Office Action mailed Sep. 9, 2009", 11 pgs.

"European Application No. 07840196.5, Office Action mailed Oct. 22, 2009", 5 pgs.

* cited by examiner

IMPLANTABLE MEDICAL DEVICE TELEMETRY WITH ADAPTIVE FREQUENCY HOPPING

CROSS-REFERENCE TO RELATED APPLICATION

This application is related to co-pending, commonly assigned, U.S. patent application Ser. No. 11/039,200, now issued as U.S. Pat. No. 7,218,969, entitled "DYNAMIC CHANNEL SELECTION FOR RF TELEMETRY WITH IMPLANTABLE DEVICE," filed on Jan. 19, 2005, and U.S. patent application Ser. No. 11/456,942, now issued as U.S. Pat. No. 7,623,922, entitled "IMPLANTABLE MEDICAL DEVICE TELEMETRY WITH PERIODIC FREQUENCY HOPPING," filed on Jul. 12, 2006, which are hereby incorporated by reference in their entirety.

TECHNICAL FIELD

This document relates generally to telemetry for implantable medical systems and particularly to a frequency agile telemetry system with adaptive frequency hopping using channel quality indicators.

BACKGROUND

Medical devices are implanted in human bodies for monitoring physiological conditions, diagnosing diseases, treating diseases, or restoring functions of organs or tissues. Examples of such implantable medical devices include cardiac rhythm management (CRM) devices, neural stimulators, neuromuscular stimulators, drug delivery devices, and biological therapy devices. When an implantable medical device is intended for long-term use in a patient, its size and power consumption are limited by implantability and longevity requirements. Consequently, many implantable medical devices depend on external systems to perform certain functions. Communication between an implantable method device and an external system is performed via telemetry. Examples of specific telemetry functions include programming the implantable medical device to perform certain monitoring or therapeutic tasks, extracting an operational status of the implantable medical device, transmitting real-time physiological data acquired by the implantable medical device, and extracting physiological data acquired by and stored in the implantable medical device.

One type of telemetry between the implantable medical device and the external system is based on inductive coupling between two closely-placed coils using the mutual inductance between these coils. One of the coils is part of the implantable medical device, and the other coil is part of the external system and is typically attached to the patient during a telemetry session. This type of telemetry is referred to as inductive telemetry or near-field telemetry because the coils must be closely situated for obtaining magnetically coupled communication.

Far-field radio-frequency (RF) telemetry provides another means for communication between the implantable medical device and the external system. The far-field RF telemetry is performed using an RF transceiver in the implantable medical device and an RF transceiver in the external system. The far-field RF telemetry frees the patient from any body surface attachment that limits mobility.

The far-field RF telemetry between the implantable medical device and the external system often operates in an environment where various sources of electromagnetic interference exist. For example, a far-filed RF telemetry link operating at a frequency within an unlicensed frequency band may be subjected to environmental interferences from various medical electronic devices, communication devices, and home electronic appliances. Such interferences may interrupt the far-filed RF telemetry link or cause errors in the data transmission.

Therefore, there is a need for ensuring the quality of far-field RF telemetry between an external system and an implanted device when interferences are present.

SUMMARY

A far-field RF telemetry system transmits data between an implantable medical device and an external system using an active channel selected from a plurality of channels each representing a frequency band within a predetermined frequency range. One or more preferred channels are identified from the plurality of channels based on channel quality indicators produced for each of the channels. When channel hopping is needed, a hop channel is selected from the one or more preferred channels and becomes the active channel.

In one embodiment, a CRM system includes an implantable medical device and an external system communicating with each other via a telemetry link. At least one of the implantable medical device and the external system includes a telemetry circuit including an antenna, a transceiver, a channel selector, a hop controller, a channel quality analyzer, and a preferred channel identifier. The transceiver transmits and receives data using at least one active channel during a telemetry session. The active channel is selected from a plurality of channels each representing a channel frequency band. The channel selector selects at least one hop channel from one or more preferred channels in response to a channel selection signal. The hop controller makes the hop channel the active channel when the hop channel is selected. The channel quality analyzer produces channel quality indicators each associated with one channel of the plurality of channels and each including at least a received signal strength indicator for that channel. The received signal strength indicator indicates the strength of signal received through a channel. The preferred channel identifier identifies the one or more preferred channels from the plurality of channels based on the channel quality indicators.

In one embodiment, a method for transmitting data between an implantable medical device and an external system via RF telemetry is provided. In response to reception of a channel selection signal, a hop channel is selected from one or more preferred channels. The hop channel is made an active channel. Data transmission between the implantable medical device and the external system is performed using the active channel. Channel quality indicators each associated with one channel of a plurality of channels are produced. Each channel of the plurality of channels represents a channel frequency band. The channel quality indicator associated with each channel includes at least a received signal strength indicator indicative of the strength of signal received through that channel. The one or more preferred channels are identified from the plurality of channels based on the channel quality indicators.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

In the drawings, which are not necessarily drawn to scale, like numerals describe similar components throughout the several views. The drawings illustrate generally, by way of example, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a frequency agile, far-field RF telemetry system for bi-directional communication between an implantable medical device and an external system. The RF telemetry system includes a plurality of channels each representing a frequency band within a predetermined frequency range. Data transmission is performed using an active channel selected from the plurality of channels. To ensure data transmission quality, the active channel hops from the current active channel to a new active channel during a telemetry session, such as when the data transmission is interrupted. This channel hopping is repeated, when necessary, until the new active channel provides for reliable and efficient data transmission. For the efficiency of the channel hopping process, the new active channel is selected from one or more preferred channels that are identified from the plurality of channels based on a channel quality analysis. This improves the chance of hopping to a "good" channel, thereby decreasing the potential number of channel hops required. The channel quality analysis results in channel quality indicators for the plurality of the channels. Each quality indicator includes one or more quality parameters for a channel and indicates whether that channel is likely to provide for reliable and efficient date transmission when used as the active channel.

While CRM systems are specifically discussed as an example, the present subject matter is applicable to any RF telemetry between an implantable medical device and an external system. The implantable medical device can be any implantable medical device capable of communicating with an external system or device via RF telemetry.

Figure 1:
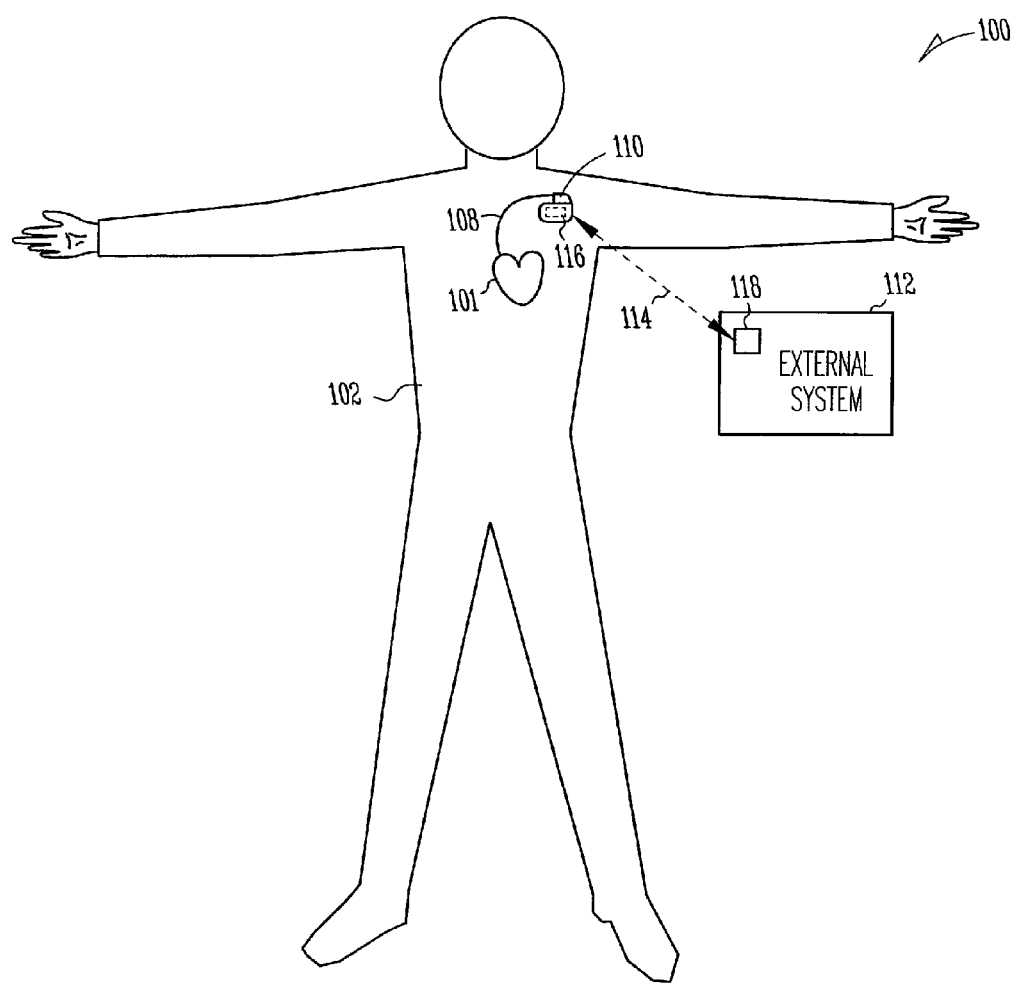
FIG. 1 is an illustration of an embodiment of a CRM system including an implantable medical device and an external system and portions of an environment in which the CRM system is used.

FIG. 1 is an illustration of an embodiment of a CRM system 100 and portions of an environment in which system 100 is used. System 100 includes an implantable medical device 110 and an external system 112. In the illustrated embodiment, after being implanted into a patient's body 102, implantable medical device 110 is coupled to the patient's heart 101 through a lead system 108. In various embodiments, implantable medical device 110 includes one or more of pacemakers, cardioverter/defibrillators, cardiac resynchronization therapy (CRT) devices, cardiac remodeling control therapy (RCT) devices, neural stimulators, drug delivery systems, biological therapy devices, and patient monitoring devices. External system 112 allows a physician or other caregiver to interact with implantable medical device 110 through a telemetry link 114, which provides for bi-directional data communication between implantable medical device 110 and external system 112.

Telemetry link 114 provides for data transmission from implantable medical device 110 to external system 112. This includes, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 110 (e.g., battery status and lead impedance). Telemetry link 114 also provides for data transmission from external system 112 to implantable medical device 110. This includes, for example, programming implantable medical device 110 to acquire physiological data, programming implantable medical device 110 to perform at least one self-diagnostic test (such as for a device operational status), and programming implantable medical device 110 to deliver at least one therapy.

Telemetry link 114 is a far-field RF telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one embodiment, a communication range of telemetry link 114 (a distance over which data is capable of being wirelessly communicated) is at least ten feet but can be as long as allowed by the communication technology utilized. Unlike an inductive telemetry link using a coil placed near implantable medical device 110, attached to the patient, and electrically connected to external system 112 with a cable, using telemetry link 114 frees the patient from any physical restraints caused by the coil and the cable and allows external system 112 to be placed entirely away from the sterile filed during an operation such as the implantation of implantable medical device 110.

Telemetry link 114 is supported by an implant telemetry module 116 of implantable medical device 110 and an external telemetry module 118 of external system 112. Implant telemetry module 116 and external telemetry module 118 form a frequency agile telemetry system that includes a plurality of channels for data transmission. These channels each represent a frequency band within a predetermined frequency range. The telemetry system uses a channel quality analysis to identify one or more preferred channels from the plurality of channels for channel hopping when needed.

The bi-directional data communication between implantable medical device 110 and external system 112 includes transmission of data frames each being a logic unit of data including a header, a payload, and a trailer. In one embodiment, the header includes a "comma," which includes a unique set of bits for signaling the beginning of receipt of a frame. A lack of comma, or failure to receive the comma, indicates a failure to receive a frame. The payload includes the data block being transmitted. The trailer includes a cyclic redundancy check (CRC) value having a value generated by a transmitter. A receiver receives that CRC value and also recalculates the CRC value based on the received data block and compares the result to the received CRC value in the trailer. The data is deemed to be correctly transmitted if the recalculated CRC value matches the received CRC value. A CRC error refers to a mismatch between the recalculated CRC value and the received CRC value. Depending on the specific communication formats, the header and the trailer each include additional information for flagging, control of data recovery, and/or synchronization between implant telemetry module 116 and external telemetry module 118. In various embodiments, data frame exchange errors, such as comma errors and CRC errors, indicate a need for channel hopping.

In one embodiment, external system 112 includes a programmer. In another embodiment, external system 112 includes a patient management system including an external device, a telecommunication network, and one or more remote devices. The external device is placed within the vicinity of implantable medical device 110 and includes external telemetry module 118 to communicate with implantable medical device 110 via telemetry link 114. The one or more remote devices are in one or more remote locations and communicate with the external device through the telecommunication network, thus allowing the physician or other caregiver to monitor and treat the patient from a distant location and/or allowing access to various treatment resources from the one or more remote locations.

Figure 2:
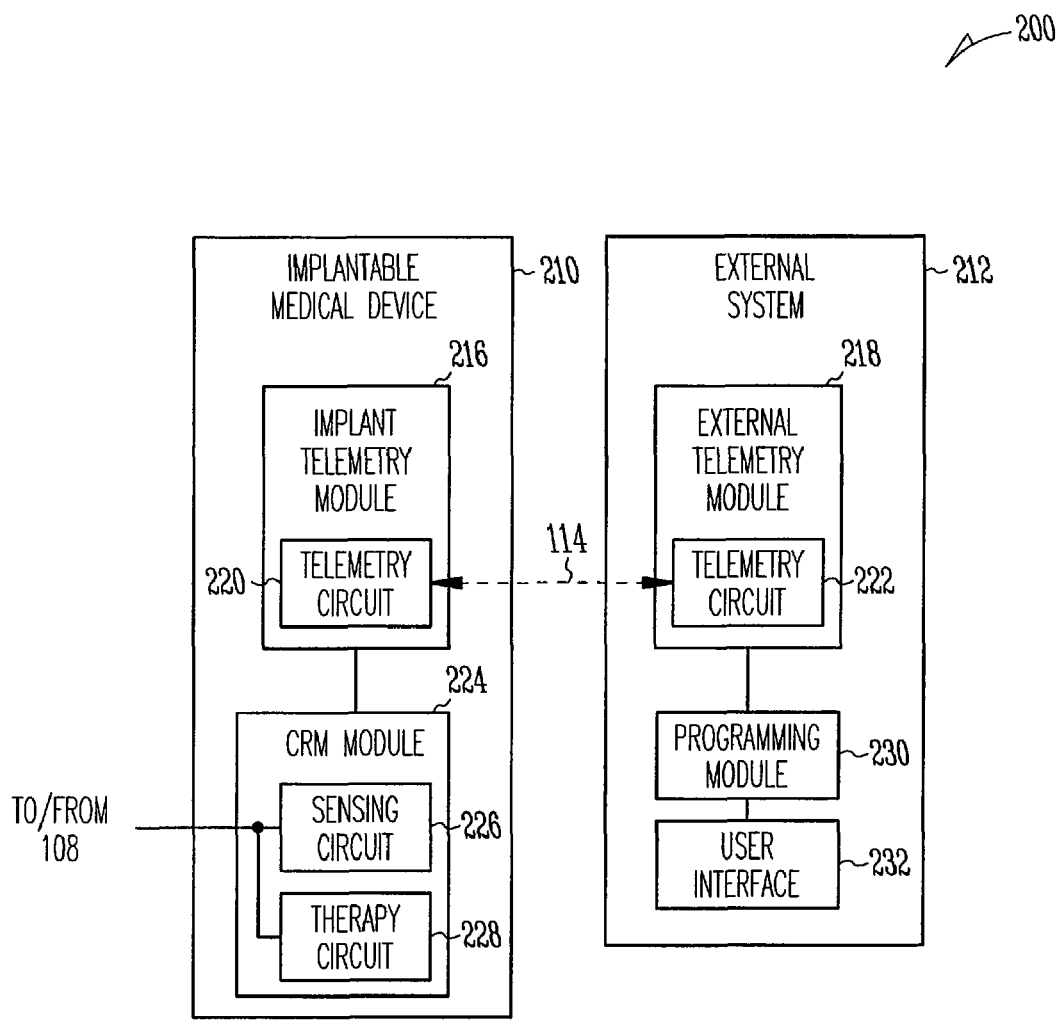
FIG. 2 is a block diagram illustrating an embodiment of a circuit of the CRM system.

FIG. 2 is a block diagram illustrating an embodiment of a circuit of a CRM system 200, which is a specific embodiment of CRM system 100. System 200 includes an implantable medical device 210, an external system 212, and telemetry link 114 providing for communication between implantable medical device 210 and external system 212.

Implantable medical device 210 is a specific embodiment of implantable medical device 110 and includes an implant telemetry module 216 and a CRM module 224. CRM module 224 includes a sensing circuit 226 that senses one or more physiological signals and a therapeutic circuit 228 that delivers one or more cardiac therapies. In various embodiments, the therapy circuit includes one or more of a pacing circuit, a cardioversion/defibrillation circuit, and any other circuit that delivers a cardiac therapy. In various embodiments, CRM module 224 further includes one or more of a drug delivery device and a biologic therapy device.

External system 212 is a specific embodiment of external system 112 and includes an external telemetry module 218, a programming module 230, and a user interface 232. Programming module 230 allows for processing of data transmitted from implantable medical device 210 via telemetry link 114 and programming of implantable medical device 210 by transmitting instructions via telemetry link 114. User interface 232 allows the physician or other caregiver to observe and analyze physiological signals and device operation data transmitted from implantable medical device 210 and to adjust the operation of implantable medical device 210.

Implant telemetry module 216 includes a telemetry circuit 220. External telemetry module 218 includes a telemetry circuit 222. Telemetry circuits 220 and 222 are discussed in detail below, with reference to FIGS. 4-7.

In various embodiments, the system elements, including various modules and circuits, described in this document are implemented by hardware, software, firmware, or any combination thereof. In various embodiments, the circuits or portions thereof described in this document are each an application-specific circuit constructed to perform one or more particular functions, a general-purpose circuit programmed to perform such function(s), or a combination thereof.

Figure 3:
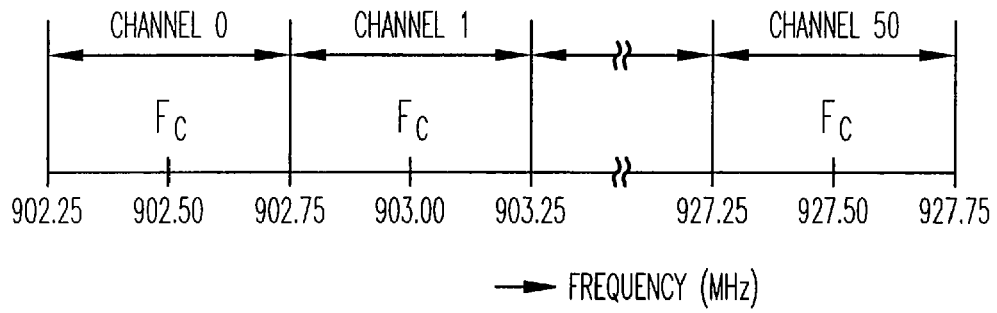
FIG. 3 is an illustration of an embodiment of telemetry channels (frequency bands) for data transmission between the implantable medical device and the external system.

FIG. 3 is an illustration of an embodiment of the plurality of channels for data transmission via telemetry link 114. The channels are distributed continuously over the predetermined frequency range. As illustrated in FIG. 3, an example of the predetermined frequency range is approximately 902.25-927.75 MHz. Each channel has a center (carrier) frequency and a bandwidth of approximately 500 kHz. Thus, the plurality of channels includes 51 channels each having a 500-kHz bandwidth within the frequency range of 902.25-927.75 MHz, within the Industrial, Scientific and Medical (ISM) band of the United States. The center frequency for each channel is approximately the mid-point of the frequency band represented by that channel. In the illustrated embodiment, Channel 0 has a frequency band of 902.25-902.75 MHz and a center frequency of 902.50 MHz, Channel 1 has a frequency band of 902.75-903.25 MHz and a center frequency of 903.00 MHz, and so forth. Other examples of the predetermined frequency range include approximately 863.0-870.0 MHz, within the Short Range Device (SRD) band of the European Union, approximately 402.0-405.0 MHz, within the worldwide Medical Implant Communication Service (MICS) band, and approximately 420.0-430.0 MHz and 440.0-450.0 MHz, within the available bands in Japan.

Figure 4:
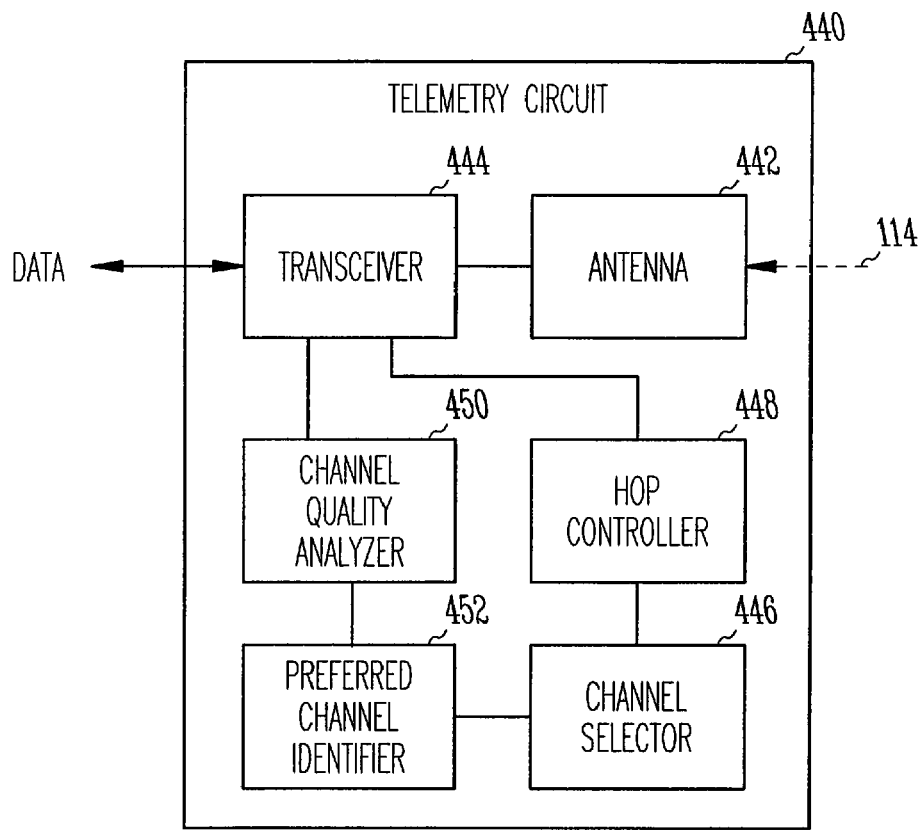
FIG. 4 is a block diagram illustrating an embodiment of a telemetry circuit of the CRM system.

FIG. 4 is a block diagram illustrating an embodiment of a telemetry circuit 440. Telemetry circuit 440 represents a specific embodiment of telemetry circuit 220 and/or telemetry circuit 222. In various embodiments, telemetry circuit 220 and telemetry circuit 222 each include a telemetry circuit with all or selected components of telemetry circuit 440, including all the embodiments of these components discussed in this document.

Telemetry circuit 440 includes an antenna 442, a transceiver 444, a channel selector 446, a hop controller 448, a channel quality analyzer 450, and a preferred channel identifier 452. Transceiver 444 transmits and receives data through antenna 442 using at least one active channel during a telemetry session. The active channel is selected from the plurality of channels. Channel selector 446 selects at least one hop channel from one or more preferred channels in response to a channel selection signal. When the hop channel is selected, hop controller 448 makes that hop channel the active channel. In one embodiment, channel selector 446 selects the hop channel from a sequence of preferred channels prioritized by a degree of preference, and the selection is made according to an order of priority. Channel quality analyzer 450 produces channel quality indicators each associated with one channel of the plurality of channels. The channel quality indicators each include one or more quality parameters each indicative of a channel quality. Preferred channel identifier 452 identifies the one or more preferred channels from the plurality of channels based on the channel quality indicators. In one embodiment, preferred channel identifier 452 identifies the one or more preferred channels by identifying one or more channel quality indicators that meet one or more predetermined requirements. In another embodiment, preferred channel identifier 452 identifies the one or more preferred channels by prioritizing channels according to their associated channel quality indicators. This results in the sequence of preferred channels prioritized by the degree of preference.

Telemetry circuit 440 allows channel hopping when needed throughout the telemetry session. Channel quality analyzer 450 produces and updates the channel quality indicators continuously, periodically, during time intervals between data frames, or according to any predetermined schedule. Preferred channel identifier 452 updates the list of the one or more preferred channels in response to any change in the channel quality indicators.

In one embodiment, external telemetry module 218 functions as a master device that controls the channel hopping in both external telemetry module 218 and implant telemetry module 216. External telemetry module 212 transmits the channel selection signal with information specifying the selected hop channel or the one or more preferred channels to implantable telemetry module 216 through telemetry link 114. This allows for synchronized channel hopping in external telemetry module 218 and implant telemetry module 216. In one embodiment, external telemetry module 218 receives at least one quality parameter of the one or more quality parameters for each channel from implant telemetry module 216. In one embodiment, the channel quality indicator for each channel includes quality parameters produced in both external telemetry module 218 and implant telemetry module 216.

Figure 5:
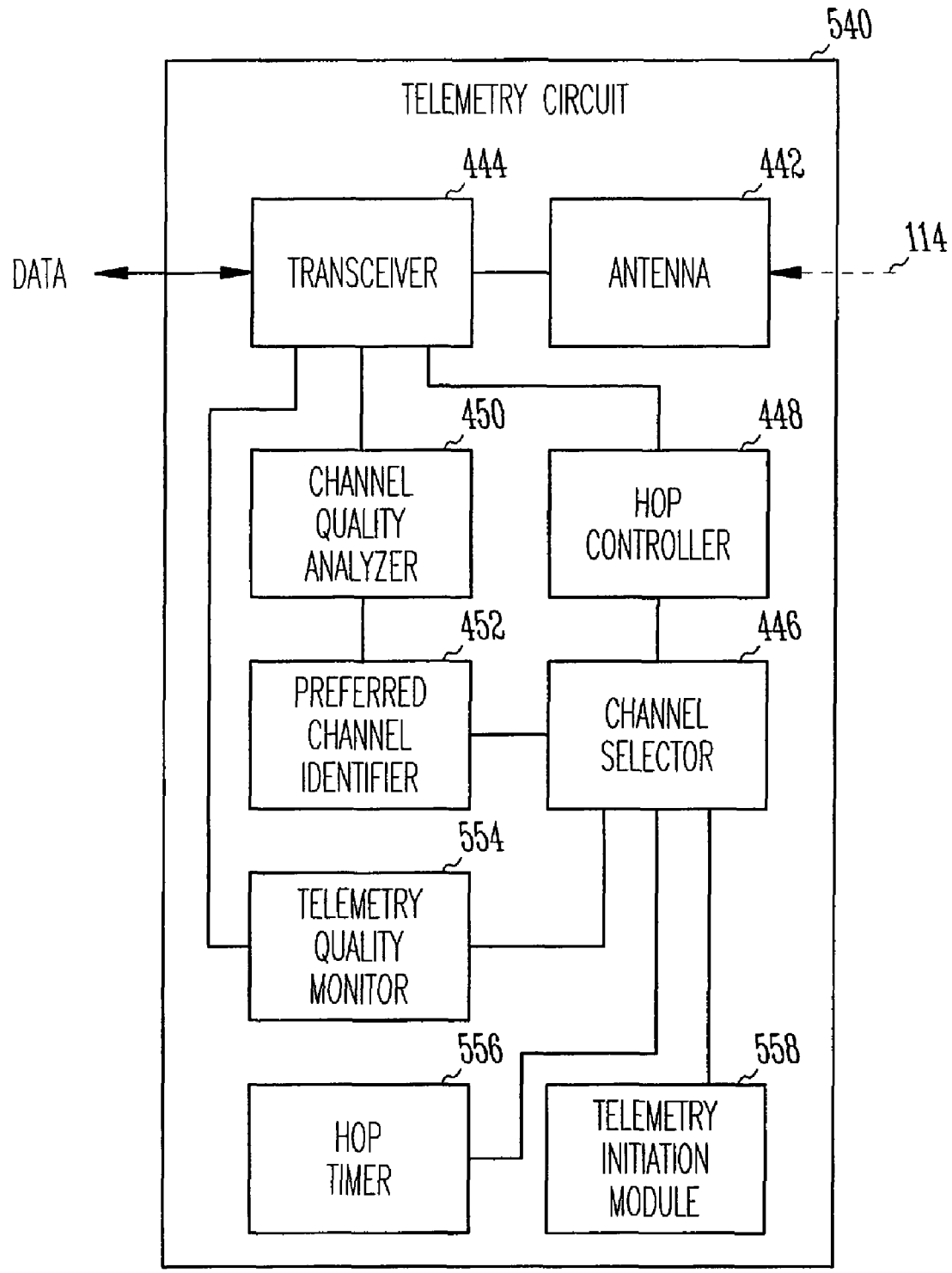
FIG. 5 is a block diagram illustrating a specific embodiment of the telemetry circuit.

FIG. 5 is a block diagram illustrating an embodiment of a telemetry circuit 540, which is a specific embodiment of telemetry circuit 440. Telemetry circuit 540 includes antenna 442, transceiver 444, channel selector 446, hop controller 448, channel quality analyzer 450, preferred channel identifier 452, a telemetry quality monitor 554, a hop timer 556, and a telemetry initiation module 558. In various embodiments, telemetry circuit 540 includes one or more of telemetry quality monitor 554, hop timer 556, and telemetry initiation module 558 to initiate each channel hopping by producing the channel selection signal.

Telemetry quality monitor 554 monitors quality of frame exchange using the active channel and produces the channel selection signal when the quality of frame exchange fails to satisfy one or more criteria. For example, the quality of frame exchange fails when a comma of a data frame is not received, or when a CRC error is detected. The channel selection signal initiates a channel hopping. If the quality of frame exchange using the hop channel (which becomes the new active channel) still fails to satisfy the one or more criteria, telemetry quality monitor 554 produces another channel selection signal to cause another channel hopping. This process is repeated until the one or more criteria are satisfied. The selection of hop channel from the one or more preferred channel potentially minimizes the number of repetitions potential required to maintain a satisfactory quality of data frame exchange. Hop timer 556 produces the channel selection signal according to a predetermined schedule. Examples of timing channel hopping based on quality of frame exchange or predetermined schedule are discussed in U.S. patent application Ser. No. 11/039,200, entitled "DYNAMIC CHANNEL SELECTION FOR RF TELEMETRY WITH IMPLANTABLE DEVICE," filed on Jan. 19, 2005, assigned to Cardiac Pacemakers, Inc., which is hereby incorporated by reference its entirety. Telemetry initiation module 558 produces the channel selection module prior to the beginning of data transmission via telemetry link 114. In one embodiment, telemetry initiation module 558 produces the channel selection signal when a telemetry session begins. In another embodiment, telemetry initiation module 558 produces the channel selection signal when telemetry circuit 540 is activated, for example, upon power-up of external system 212.

Figure 6:
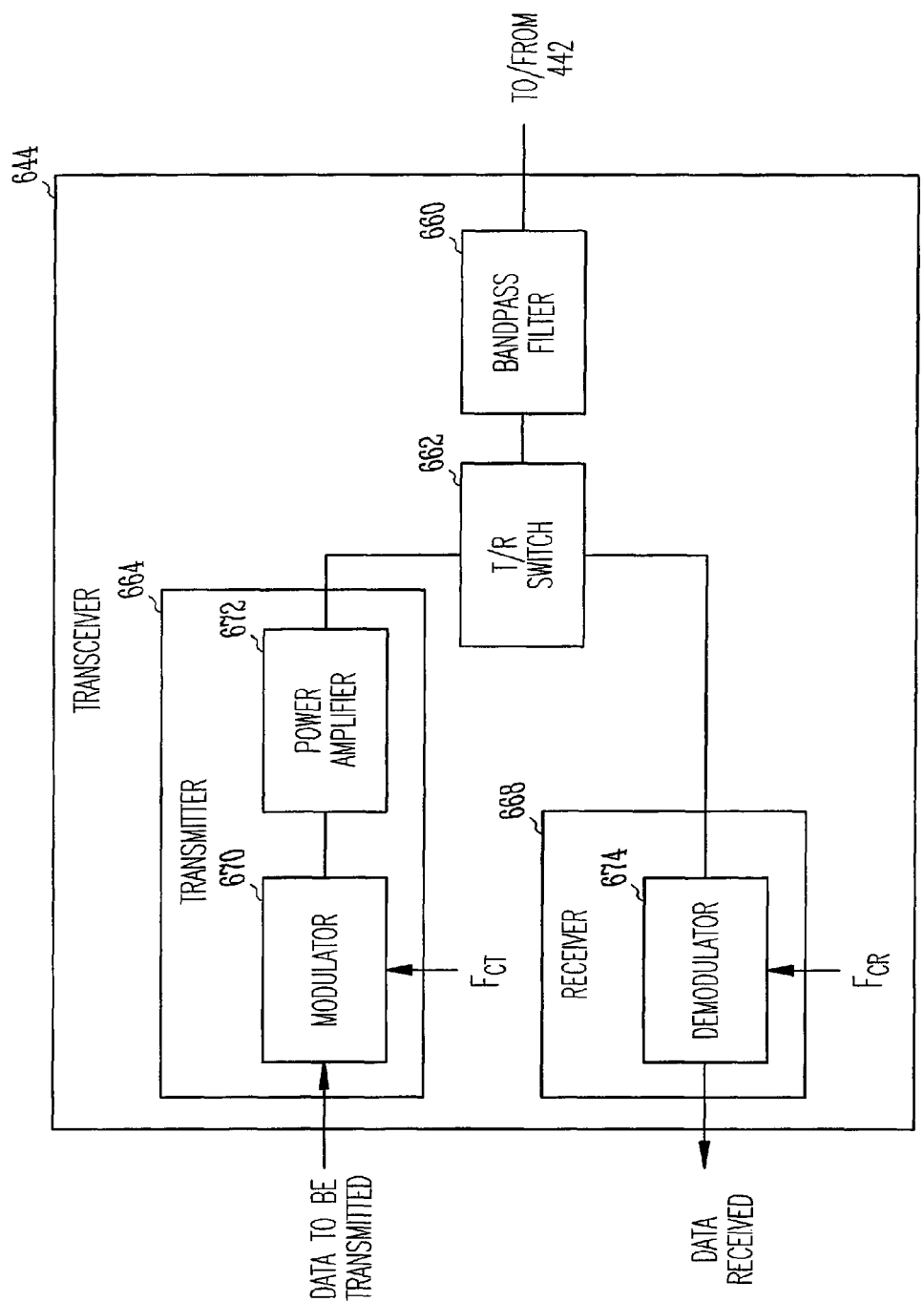
FIG. 6 is a block diagram illustrating an embodiment of a transceiver of the telemetry circuit.

FIG. 6 is a block diagram illustrating an embodiment of a transceiver 644, which is a specific embodiment of transceiver 444. Transceiver 644 includes a band-pass filter 660, a transmit/receive (T/R) switch 662, a transmitter 664, and a receiver 668. Band-pass filter 660 has a pass band corresponding to the predetermined frequency range within which the channels are distributed. For example, if the predetermined frequency range is the ISM band of 902-928 MHz, the pass band of band-pass filter 660 is approximately 902-928 MHz. T/R switch 662 provides a connection between antenna 442 and one of transmitter 664 and receiver 668 at a time, such that the data transmission via telemetry link 114 is unidirectional at any instant. Transmitter 664 transmits data using an active transmission channel and includes a modulator 670 and a power amplifier 672. Modulator 670 modulates a carrier signal with data to be transmitted. The carrier signal has a frequency being the center frequency of the active transmission channel ($F_{CT}$). Power amplifier 672 amplifies the modulated carrier for transmission over telemetry link 114. Receiver 668 receives data using an active receiving channel and includes a demodulator 674. Demodulator 674 demodulates the received signal to recover to data received. Receiver 668 receives a signal that is a carrier signal modulated with the data received. The carrier signal has a carrier frequency being the center frequency of the active receiving channel ($F_{CR}$). In one embodiment, the active transmission channel and the active receiving channel include substantially identical channel frequency bands (i.e., $F_{CT}$ and $F_{CR}$ are approximately equal). In another embodiment, the active transmission channel and the active receiving channel include substantially different channels (i.e., $F_{CT}$ and $F_{CR}$ are substantially different). The active transmission channel and the active receiving channel are selected from the plurality of channels. The discussion in this document regarding the "active channel" applies to each of the active transmission channel and the active receiving channel.

Figure 7:
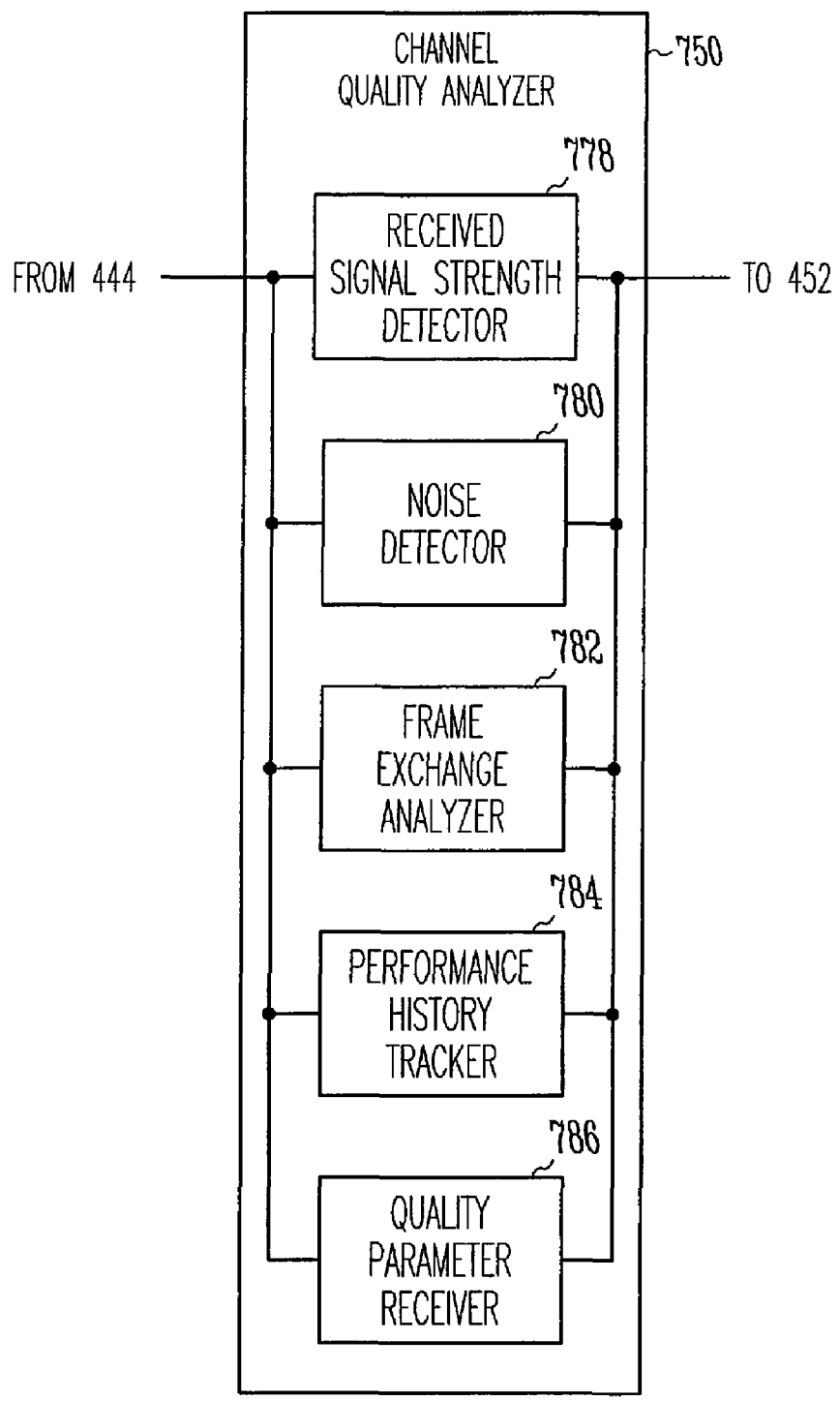
FIG. 7 is a block diagram illustrating an embodiment of a channel quality analyzer of the telemetry circuit.

FIG. 7 is a block diagram illustrating an embodiment of a channel quality analyzer 750, which is a specific embodiment of channel quality analyzer 450. In the illustrated embodiment, channel quality analyzer 750 includes a received signal strength detector 778, a noise detector 780, a frame exchange analyzer 782, a performance history tracker 784, and a quality parameter receiver 786. In various embodiments, channel quality analyzer 750 includes one or more of received signal strength detector 778, noise detector 780, frame exchange analyzer 782, performance history tracker 784, and quality parameter receiver 786, depending on various design considerations and/or performance requirements, including whether channel quality analyzer 750 is part of the telemetry circuit of implant telemetry module 216 or part of the telemetry circuit of external telemetry module 218. In other words, channel quality analyzer 750 produces channel quality indicators each including one or more quality parameters produced by one or more of received signal strength detector 778, noise detector 780, frame exchange analyzer 782, performance history tracker 784, and quality parameter receiver 786. In various embodiments, channel quality analyzer 750 includes two or more of received signal strength detector 778, noise detector 780, frame exchange analyzer 782, performance history tracker 784, and quality parameter receiver 786, and preferred channel identifier 452 identifies the one or more preferred channels using channel quality indicators each weighted by applying a predetermined weighting factor. The channel quality indicators are produced by the two or more of received signal strength detector 778, noise detector 780, frame exchange analyzer 782, performance history tracker 784, and quality parameter receiver 786. The channel quality indicator produced by each of received signal strength detector 778, noise detector 780, frame exchange analyzer 782, performance history tracker 784, and quality parameter receiver 786 are given a predetermined weighting factor.

Received signal strength detector 778 produces received signal strength indicators each associated with one channel of the plurality of channels and indicative of the strength of signal received through that channel. In one embodiment, the received signal strength indicator associated with a channel is the amplitude of the RF signal received using that channel. In one embodiment, preferred channel identifier 452 identifies the one or more preferred channels from the plurality of channels based on the received signal strength indicators. In a specific embodiment, preferred channel identifier 452 identifies the one or more preferred channels from the plurality of channels by comparing the received signal strength indicators to a predetermined threshold. In another specific embodiment, preferred channel identifier 452 produces the sequence of preferred channels by prioritizing channels according to their associated received signal strength indicators.

Noise detector 780 produces noise floor indicators each associated with one channel of the plurality of channels and indicative of a noise floor of that channel. In one embodiment, noise detector 780 produces the noise floor indicators by measuring a noise level associated with each channel of the plurality of channels when external system 212 is not communicatively coupled with implantable medical device 210, such as before the telemetry session begins. In another embodiment, noise detector 780 produces the noise floor indicators by measuring a noise level associated with each channel of the plurality of channels when no data is being transmitted between external system 212 and implantable medical device 210 through that channel. In one embodiment, preferred channel identifier 452 identifies the one or more preferred channels from the plurality of channels based on the noise floor indicators. In a specific embodiment, preferred channel identifier 452 identifies the one or more preferred channels from the plurality of channels by comparing the noise floor indicators to a predetermined threshold. In another embodiment, preferred channel identifier 452 produces the sequence of preferred channels by prioritizing channels according to their associated noise floor indicators.

Frame exchange analyzer 782 produces frame exchange metrics each associated with one channel of the plurality of channels. In one embodiment, preferred channel identifier 452 identifies the one or more preferred channels from the plurality of channels based on the frame exchange metrics. In a specific embodiment, preferred channel identifier 452 identifies the one or more preferred channels from the plurality of channels by comparing the frame exchange metrics to a predetermined threshold. In another specific embodiment, preferred channel identifier 452 produces the sequence of preferred channels by prioritizing channels according to their associated frame exchange metrics. In one embodiment, the frame exchange metrics each include a success ratio being a ratio of the number of successful frame exchanges to a total number of frame exchanges. Frame exchange analyzer 782 calculates success ratios each associated with one channel of the plurality of channels. Preferred channel identifier 452 identifies the one or more preferred channels from the plurality of channels by comparing the success ratios to a predetermined threshold or by prioritizing channels according to their associated success ratios.

Performance history tracker 784 produces performance history indicators each associated with one channel of the plurality of channels and indicative of a history of at least one of the one or more quality parameters indicative of the channel quality of that channel. Examples of the one or more quality parameters include the received signal strength indicators, the noise floor indicators, and the frame exchange metrics discussed above. In one embodiment, preferred channel identifier 452 identifies the one or more preferred channels from the plurality of channels based on the performance history indicators. In a specific embodiment, preferred channel identifier 452 identifies the one or more preferred channels from the plurality of channels by comparing the performance history indicators to a predetermined threshold. In another embodiment, preferred channel identifier 452 produces the sequence of preferred channels by prioritizing channels according to their associated performance history indicators.

Quality parameter receiver 786 receives quality parameters produced and transmitted at the other side of telemetry link 114. The received quality parameters include one or more of the received signal strength indicators, the noise floor indicators, the frame exchange metrics, and the performance history indicators discussed above. In one embodiment, preferred channel identifier 452 identifies the one or more preferred channels from the plurality of channels based on the received quality parameters. In a specific embodiment, preferred channel identifier 452 identifies the one or more preferred channels from the plurality of channels by comparing the received quality parameters to a predetermined threshold. In another embodiment, preferred channel identifier 452 produces the sequence of preferred channels by prioritizing channels according to their associated received quality parameters. In one embodiment, quality parameter receiver 786 of external system 212 receives one or more quality parameters produced by and transmitted from implantable medical device 210.

In one embodiment, channel quality analyzer 750 produces other quality parameters such as signal-to-noise ratios (SNRs) each associated with one channel of the plurality of channels. For example, SNRs are calculated as the ratio of the received signal strength indicator to the noise floor indicator for each channel. In general, channel quality indicators produced by channel quality analyzer 750 may include any one or more quality parameters that potentially indicate the efficiency and accuracy of data transmission via telemetry link 114.

In one embodiment, implant telemetry module 216 and external telemetry module 218 each include a channel quality analyzer that includes some or all of the elements of channel quality analyzer 750 as illustrated in FIG. 7. In one embodiment, the channel quality analyzer of implant telemetry module 216 includes received signal strength detector 778, while the channel quality analyzer of external telemetry module 218 includes all of received signal strength detector 778, noise detector 780, frame exchange analyzer 782, performance history tracker 784, and quality parameter receiver 786. Quality parameter receiver 786 receives the received signal strength indicators produced by and transmitted from implant telemetry module 216. Preferred channel identifier 452 of external telemetry module 218 identifies the one or more preferred channels from the plurality of channels based on one or more of the received signal strength indicators (produced by external telemetry module 218), the noise floor indicators, the frame exchange metrics, the performance history indicators, and the received quality parameters (the received signal strength indicators produced by implant telemetry module 216).

In one embodiment, channel quality analyzer 750 produces channel quality indicators each include multiple quality parameters that are used to select the one or more preferred channels at different stages of data transmission. In one embodiment, when telemetry circuit 540 is powered up, or prior to the start of a telemetry session, preferred channel identifier 452 identifies the one or more preferred channels from the plurality of channels based on the performance history indicators. This is particularly useful if system 200 is used repeatedly in the same environment, such as the same room in a hospital or the same room in the patient's home. In one embodiment, prior to the start of a telemetry session, preferred channel identifier 452 identifies the one or more preferred channels from the plurality of channels based on the noise floor indicators produced when no data transmission is performed via telemetry link 114. In various embodiments, preferred channel identifier 452 identifies the one or more preferred channels from the plurality of channels based on either or both of the received signal strength indicators and the frame exchange metrics continuously, periodically, or according to a predetermined schedule during the telemetry session.

Figure 8:
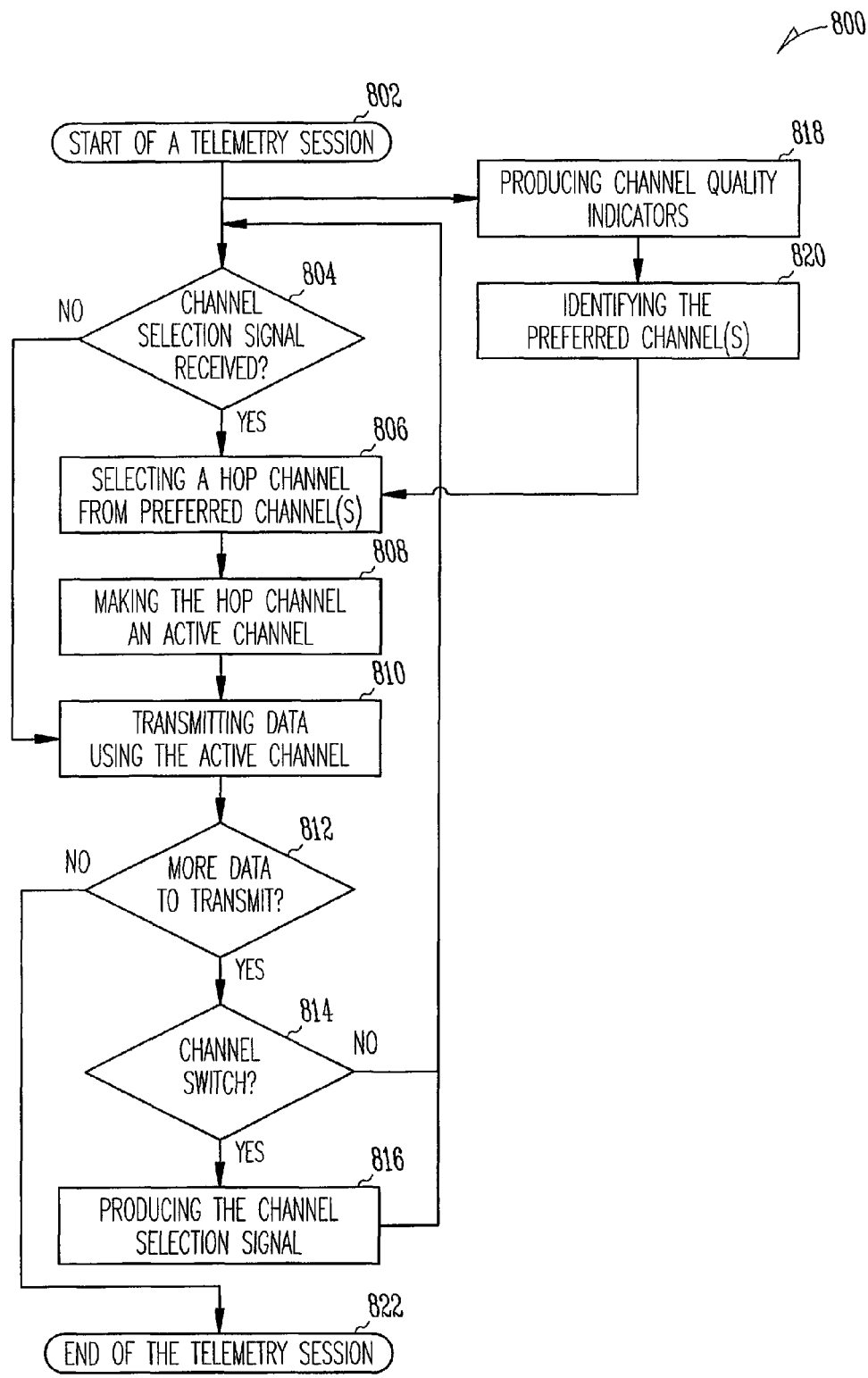
FIG. 8 is a flow chart illustrating a method for transmitting data between an implantable medical device and an external system.

FIG. 8 is a flow chart illustrating a method 800 for transmitting data between an implantable medical device and an external system. In one embodiment, method 800 is performed by system 100, including its specific embodiment system 200 and various embodiments of the elements of system 200 discussed above.

A telemetry session is started at 802. Bi-directional data transmission is performed via a telemetry link between an implantable medical device and an external system during the telemetry session. The telemetry link includes a plurality of channels each representing a channel frequency band within a predetermined frequency range. At least one active channel is selected from the plurality of channels for the data transmission at any instant during the telemetry session.

If a channel selection signal is received at 804, a hop channel is selected from one or more preferred channels of the plurality of channels at 806. In various embodiments, the channel selection signal is produced when the telemetry session begins, when the telemetry link is activated, according to a predetermined schedule, or when the quality of data transmission through the telemetry link fails to satisfy one or more criteria. In one embodiment, the one or more preferred channels are prioritized by a degree of preference, and the hop channel is selected based on the priority. The hop channel is made the active channel at 808. Data are transmitted between the implantable medical device and the external system using the active channel at 810.

If the channel selection signal is not received at 804, no channel hopping is needed. The data are transmitted between the implantable medical device and the external system using a current active channel at 810.

In one embodiment, two substantially distinctive active channels are used for data transmission in the two directions (one from the implantable medical device to the external system, and the other from the external system to the implantable medical device). In one embodiment, channel hopping with respect to each of the two substantively distinctive active channels is controlled separately using method 800 and performed in parallel during the telemetry session.

The telemetry session ends at 822 when all the data intended to be transmitted during the telemetry session are transmitted at 812. If more data are to be transmitted at 812, and the active channel is to be switched to another channel at 814, the channel selection signal is produced at 816. The data transmission then continues after channel hopping. If more data are to be transmitted at 812, but the active channel is not to be switched to another channel at 814, the data transmission then continues using the current active channel, i.e., without channel hopping. In various embodiments, the active channel is to be switched to another channel at 814 according to the predetermined schedule, or when the quality of data transmission through the telemetry link fails to satisfy one or more criteria.

During the telemetry session, channel quality indicators each associated with one channel of the plurality of channels are produced at 818. The channel quality indicator for a channel includes one or more quality parameters indicative of quality of that channel. The one or more preferred channels are identified from the plurality of channels based on the channel quality indicators at 820. Steps 818 and 820 are performed continuously, periodically, or according a predetermined schedule during the telemetry session to maintain an updated list or sequence of the one or more preferred channels for the hop channel selection at 806. In one embodiment, the one or more preferred channels are identified from the plurality of channels at 820 by identifying one or more of the channel quality indicators that meet one or more predetermined requirements. In another embodiment, the sequence of preferred channels is produced at 820 by prioritizing channels according to their associated channel quality indicators.

Examples of the one or more quality parameters include received signal strength indicators each indicative of the strength of signal received through a channel, noise floor indicators each indicative of the noise floor of a channel, frame exchange metrics such as the success ratios each being a ratio of the number of successful frame exchanges to a total number of frame exchanges performed using a channel, and performance history indicators each indicative of data transmission performance history of a channel. The data transmission performance history is represented by the history of one or more of the received signal strength indicators, the noise floors, and the frame exchange metrics. In one embodiment, the one or more quality parameters include at least one quality parameter produced at the other side of the telemetry link. For example, the implantable medical device produces the received signal strength indicators each indicative of the strength of signal received by the implantable medical device through a channel. The received signal strength indicators are transmitted to the external system. The external system controls the channel hopping in both the implantable medical device and the external system using the one or more preferred channels identified using one or more quality parameters including the received signal strength indicators produced by the implantable medical device.

It is to be understood that the above detailed description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A cardiac rhythm management (CRM) system, comprising an external system to communicate with an implantable medical device, the external system including:
   a telemetry circuit including:
      a transceiver adapted to transmit and receive data using at least one active radio frequency (RF) channel, the at least one active RF channel selectable from a plurality of RF channels available for use by the transceiver, each of the RF channels representing a channel frequency band;
      a channel selector coupled to the transceiver, the channel selector adapted to select at least one hop channel according to a sequence of prioritized RF channels;
      a hop controller coupled to the channel selector, the hop controller adapted to make the at least one hop channel the active RF channel when the at least one hop channel is selected;
      a channel quality analyzer coupled to the channel selector and adapted to produce an RF channel quality indicator for an RF channel, wherein the RF channel quality indicator includes at least a received signal strength indicator indicative of a strength of signal received through that channel, wherein the channel quality analyzer includes a quality parameter receiver configured to receive an RF channel quality indicator produced by a channel quality analyzer of the implantable medical device; and
      a preferred channel identifier coupled to the channel quality analyzer, the preferred channel identifier adapted to prioritize the plurality of channels according to the produced and received RF channel quality indicators into the sequence of prioritized RF channels.

2. The system of claim 1, wherein the at least one active channel comprises an active transmission channel selected from the plurality of channels and an active receiving channel selected from the plurality of channels, the active transmission channel and the active receiving channel representing substantially different channel frequency bands, and the transceiver comprises:
   a transmitter to transmit data using the active transmission channel;
   a receiver to receive data using the active receiving channel; and
   a transmit/receive switch to provide a connection between the antenna and one of the transmitter and the receiver.

3. The system of claim 1, wherein the telemetry circuit further comprises a telemetry quality monitor adapted to monitor quality of data transmission associated with the active channel and to produce the channel selection signal when the quality of data transmission fails to satisfy one or more criteria.

4. The system of claim 1, wherein the telemetry circuit further comprises a hop timer to produce the channel selection signal according to a predetermined schedule.

5. The system of claim 1, wherein the telemetry circuit further comprises a telemetry initiation module to produce the channel selection signal when or before the telemetry session begins.

6. The system of claim 1, wherein the channel quality indicators comprise noise floor indicators each associated with one channel of the plurality of channels and indicative of a noise floor of that channel, the channel quality analyzer comprises a noise detector adapted to produce the noise floor indicators, and the preferred channel identifier is adapted to identify the sequence of preferred channels from the plurality of channels using at least the received signal strength indicators and the noise floor indicators.

7. The system of claim 6, wherein the noise detector is adapted to produce the noise floor indicators by measuring a noise level associated with each channel of the plurality of channels when the external system is not communicatively coupled with the implantable medical device.

8. The system of claim 6, wherein the noise detector is adapted to produce the noise floor indicators by measuring a noise level associated with each channel of the plurality of channels when no data is being transmitted between the external system and the implantable medical device through that channel.

9. The system of claim 1, wherein the channel quality indicators comprise frame exchange metrics each associated with one channel of the plurality of channels, the channel quality analyzer comprises a frame exchange analyzer adapted to produce the frame exchange metrics, and the preferred channel identifier is adapted to identify the sequence of preferred channels from the plurality of channels using at least the received signal strength indicators and the frame exchange metrics.

10. The system of claim 9, wherein the frame exchange analyzer comprises a success ratio producer adapted to calculate success ratios each associated with one channel of the plurality of channels, the success ratios each being a ratio of a number of successful frame exchanges to a total number of frame exchanges.

11. The system of claim 1, wherein the channel quality indicators comprise performance history indicators each associated with one channel of the plurality of channels and indicative of a history of the channel quality indicator of that channel, the channel quality analyzer comprises a performance history tracker adapted to produce the performance history indicators, and the preferred channel identifier is adapted to identify the sequence of preferred channels from the plurality of channels using at least the received signal strength indicators and the performance history indicators.

12. The system of claim 1, wherein the external telemetry module comprises the telemetry circuit, and wherein the channel selector is adapted to transmit data specifying one or more of the at least one hop channel and the sequence of preferred channels to the implantable medical device through the telemetry link.

13. The system of claim 12, wherein the quality parameter receiver is configured to receive at least one quality parameter of each of the channel quality indicators from the implantable medical device.

14. The system of claim 1, wherein the plurality of channels are distributed over one of a first frequency range of approximately 902.25-927.75 MHz, a second frequency range of approximately 863-870 MHz, and a third frequency range of approximately 402-405 MHz.

15. The system of claim 6, wherein the channel quality analyzer is adapted to produce signal-to-noise ratios each associated with one channel of the plurality of channels, the signal-to-noise ratios each being a ratio of the received signal strength indicator to the noise floor indicator for the one channel.

16. The system of claim 1, wherein the preferred channel identifier is adapted to identify the sequence of preferred channels from the plurality of channels using the received signal strength indicators and one or more of:
   noise floor indicators each associated with one channel of the plurality of channels and indicative of a noise floor of that channel;

frame exchange metrics each associated with one channel of the plurality of channels and indicative of a ratio of a number of successful frame exchanges to a total number of frame exchanges for that channel; and performance history indicators each associated with one channel of the plurality of channels and indicative of a history of the channel quality indicator of that channel.

17. The system of claim 16, wherein the preferred channel identifier is adapted to identify the sequence of preferred channels from the plurality of channels using the received signal strength indicators and the one or more of the noise floor indicators, the frame exchange metrics, and the performance history indicators each weighted by applying a predetermined weighting factor.

18. The system of claim 16, wherein the external telemetry module comprises the telemetry circuit, and the channel quality analyzer comprises a quality parameter receiver adapted to receive quality parameters from the implantable medical device, the received quality parameters including one or more of the received signal strength indicators, the noise floor indicators, the frame exchange metrics, and the performance history indicators.

19. The system of claim 16, wherein the preferred channel identifier is adapted to identify the sequence of preferred channels from the plurality of channels using the received signal strength indicators and the noise floor indicators or the performance history indicators prior to a start of the telemetry session when no data is being transmitted between the external system and the implantable medical device.

20. The system of claim 19, wherein the preferred channel identifier is adapted to identify the sequence of preferred channels from the plurality of channels using the received signal strength indicators and the frame exchange metrics during the telemetry session.

21. The system of claim 1, wherein the channel quality analyzer comprises:

a quality parameter receiver adapted to receive a second received signal strength indicator, produced by the implantable medical device, indicative of a strength of signal received through the channel, and wherein the preferred channel identifier is adapted to prioritize the plurality of channels according to quality as indicated by the first and second received signal strength indicators, into the sequence of prioritized RF channels.

\* \* \* \* \*